United States Patent [19]
Hawkins

[11] Patent Number: 5,538,514
[45] Date of Patent: Jul. 23, 1996

[54] METHOD FOR FORMING BONE CEMENT TO AN IMPLANT

[75] Inventor: Michael E. Hawkins, Columbia City, Ind.

[73] Assignee: Zimmer, Inc., Warsaw, Ind.

[21] Appl. No.: 224,381

[22] Filed: Apr. 7, 1994

[51] Int. Cl.$^6$ ............................................. A61F 2/28
[52] U.S. Cl. ................................................. 623/16; 606/92
[58] Field of Search ................................. 623/16; 606/92, 606/93, 94; 433/180, 226

[56] References Cited

U.S. PATENT DOCUMENTS

| | | | |
|---|---|---|---|
| 4,141,864 | 2/1979 | Rijke et al. .................. | 606/92 X |
| 4,244,689 | 1/1981 | Ashman ........................ | 433/175 |
| 4,281,420 | 8/1981 | Raab . | |
| 4,341,691 | 7/1982 | Anuta ........................... | 523/116 |
| 4,365,359 | 12/1982 | Raab ............................. | 623/22 X |
| 4,374,936 | 2/1983 | Tomioka et al. ............. | 523/116 |
| 4,412,015 | 10/1983 | Lustgarten et al. .......... | 523/116 |
| 4,542,167 | 9/1985 | Aoki ............................. | 523/109 |
| 4,550,136 | 10/1985 | Hosch .......................... | 524/718 |
| 4,554,686 | 11/1985 | Baker .......................... | 623/16 |
| 4,574,130 | 3/1986 | Potter et al. ................. | 523/111 |
| 4,593,064 | 6/1986 | Hosch .......................... | 524/718 |
| 4,645,503 | 2/1987 | Lin et al. ..................... | 623/16 |
| 4,668,295 | 5/1987 | Bajpai .......................... | 106/85 |
| 4,678,436 | 7/1987 | Kondo et al. ................. | 433/228 |
| 4,718,910 | 1/1988 | Draenert ....................... | 623/16 |
| 4,791,150 | 12/1988 | Braden et al. ................ | 523/117 |
| 4,808,184 | 2/1989 | Tepic ............................ | 604/56 |
| 4,812,120 | 3/1989 | Flanagan et al. ............ | 433/173 |
| 4,813,876 | 3/1989 | Wang ............................ | 623/16 X |
| 4,886,843 | 12/1989 | Walton ........................ | 522/174 |
| 5,189,077 | 2/1993 | Kerby ............................ | 533/116 |
| 5,276,070 | 1/1994 | Arroyo .......................... | 523/117 |

OTHER PUBLICATIONS

"Initiation of Polymerization with High–Energy Radiation," Vivian Stannett and Joseph Silverman, 1983, pp. 435–447.

*Primary Examiner*—Mary Beth O. Jones
*Attorney, Agent, or Firm*—Todd A. Dawson

[57] ABSTRACT

A method for molding bone cement to a prosthetic implant in which a cement mixture absent any amine initiators is molded about the implant and polymerization is initiated by exposing the cement mixture to a radiation source. The method eliminates the manufacturing timing problems of molding a polymerizing bone cement mixture to an implant.

3 Claims, 3 Drawing Sheets

METHOD FOR FORMING BONE CEMENT TO AN IMPLANT

This invention relates to a method of forming bone cement to a prosthetic implant and has specific relevance to a method for forming bone cement to an implant and initiating polymerization by exposing the cement to radiation within the electromagnetic spectrum.

BACKGROUND OF INVENTION

Bone cement is commonly used to attach a prosthetic implant such as a hip stem to living bone tissue such as a prepared intramedullary canal of a femur. Bone cements are typically acrylic polymeric materials which undergo polymerization when thoroughly mixed together. The preferred conventional bone cement is composed of a powder, polymethyl methacrylate (PMMA) polymer and a liquid, methyl methacrylate (MMA) monomer. The polymerization requires an initiator to catalyze hardening. The initiator is typically a tertiary amine such as aniline or toluidine. The amine initiator cleaves the benzoyl peroxide in the PMMA powder component to produce the free radicals which initiate the bonding of the liquid monomer.

In a surgical application, the bone cement may be contaminated by blood, body fluids, water, and air bubbles which weaken the interlock between the bone tissue and implant. Prosthetic implants have been developed which include an outer layer of cement molded to the implant. By molding a layer of cement to the implant in a controlled environment, the interlock between the implant and cement is greatly improved. During the implant procedure, an additional amount of bone cement is used to secure the implant to the bone tissue. The additional bone cement interacts molecularly with the layer of cement molded to the implant and interdigitates with the bone tissue to provide a positive interlock.

Molding or applying bone cement to metal or composite prosthetic implants presents a variety of production difficulties. The bone cement must be applied to the implant to reduce the number of contaminants and voids as much as possible to ensure a positive interlock between the implant and cement. In an a preferred manufacturing setting, the cement is applied by a molding process. The implant is placed in a mold and the cement is mixed and extruded into the mold where it is polymerized around the implant. Extruding polymerizing bone cement into a mold, however, is problematic. The viscosity of acrylic cements increases with the time elapsed after mixing the monomer and polymer components. In an extrusion process, the bone cement, after mixture, quickly becomes too stiff to be easily extruded into the molds. In addition, the amine initiators in the cement which initiate polymerization discolor during sterilization, turning yellow or brown in color.

SUMMARY OF INVENTION

The method of this invention eliminates the extrusion problems of molding bone cement to implants by eliminating the need for an amine initiator in the cement mixture. In this method, radiation exposure is used to initiate polymerization of the liquid monomer. By eliminating the amine initiators, the viscosity of the cement mixture remains the same until radiated. Consequently, the liquid monomer and powder polymer can be pre-mixed and freely extruded into the mold from a batch container without any change in the viscosity. Eliminating the amine initiator also eliminates the discoloration problem which occurs during the sterilization of the implant.

The cement mixture absent any amine initiators can be applied or molded to the implant manually or in an automated process. Preferably in a manufacturing setting, the cement is applied to the implant in an automated extrusion process using conventional extrusion equipment and techniques. The individual implants are placed in a mold and the cement mixture is injected into the mold cavity under pressure to eliminate any voids. The cement mixture remains stable and viscous until the implant and cement mixture inside the mold are exposed to a radiation source. Radiating the liquid monomer with relatively low energy X-rays or relatively high energy gamma rays produces free radicals in the monomer which begins the polymerization inside the mold. Once the monomer is completely polymerized or cured, the implant is removed from the mold and is ready for sterilization and packaging. In another variation of the method, a photosensitive initiator is added to the liquid monomer. The mixture is exposed to a light source to initiate polymerization as the mixture flows into the mold. A transparent mold may also be used so that the mixture can be exposed to the light source after the introduction of the cement mixture into the mold.

It should be understood that the cement mixture could be applied topically to an implant or used as an adhesive to affix a thick layer of cement to an implant.

Accordingly, an advantage of this invention is to provide a method of forming bone cement to a prosthetic implant in which a cement mixture absent any amine initiators is placed on the implant and polymerization is initiated by exposing the cement mixture to a radiation source to adhere the cement to the implant.

Another advantage is to provide a method of forming an acrylic bone cement to a prosthetic implant which eliminates the need for an amine initiator in the cement mixture.

Another advantage is to provide a method of forming an acrylic cement to an implant wherein the cement mixture remains flowable until exposure to a radiation source initiates polymerization.

Other advantages will become apparent upon a reading of the following description.

BRIEF DESCRIPTION OF THE DRAWINGS

The preferred embodiments of this invention have been depicted for illustrative purposes only wherein.

DESCRIPTION OF THE PREFERRED EMBODIMENT

The preferred embodiments herein described are not intended to be exhaustive or to limit the invention to the precise form disclosed. They are chosen and described to explain the principles of the invention and their application and practical use to enable others skilled in the art to utilize their teachings.

Figure 1:
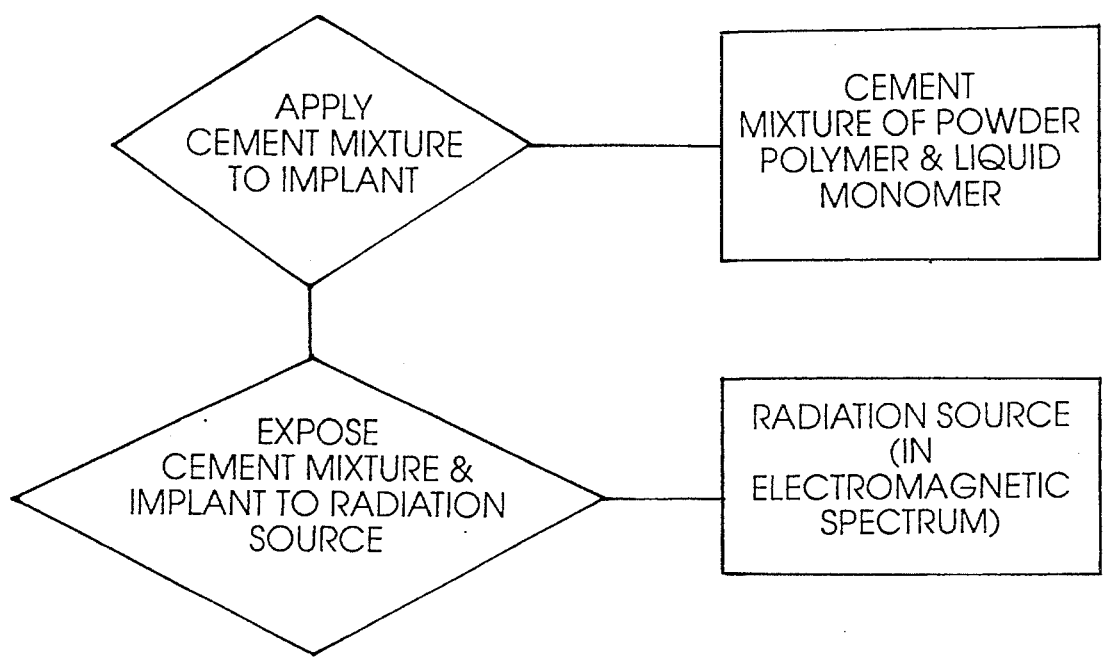
FIG. 1 is a flow chart of the method of polymerizing a bone cement about a prosthetic implant of this invention.

As shown in FIG. 1, the method of this invention uses radiation to initiate the polymerization of a bone cement in the application or molding of the cement to a prosthetic implant. The method uses a bone cement absent any tertiary amine initiators. The cement mixture includes a powder polymer and a liquid monomer. The liquid monomer preferably methyl methacrylate (MMA) is formulated to contain no amine initiators such as aniline or toluidine including N,N'-dimethyl p-toluidine or dihydroxyethyl-o-toluidine. The powder polymer is preferably polymethyl methacrylate (PMMA). Optionally, the powder polymer may contain a styrene copolymer. It should be noted that the mixture of the liquid monomer and powder polymer is stable and will retain its viscosity for an extended period of time.

The cement mixture can be applied to the implant manually or in an automated process. Preferably in a manufacturing setting, the cement mixture is applied to the implant in an extrusion process using conventional extrusion equipment and techniques. Extrusion equipment and devices suitable for extruding the bone cement mixture as described about prosthetic implants are well known in the art. Conventional extrusion equipment generally includes a mold, a hopper in which the cement mixture is contained, and an injector which forces the cement mixture into the mold.

Figure 2:
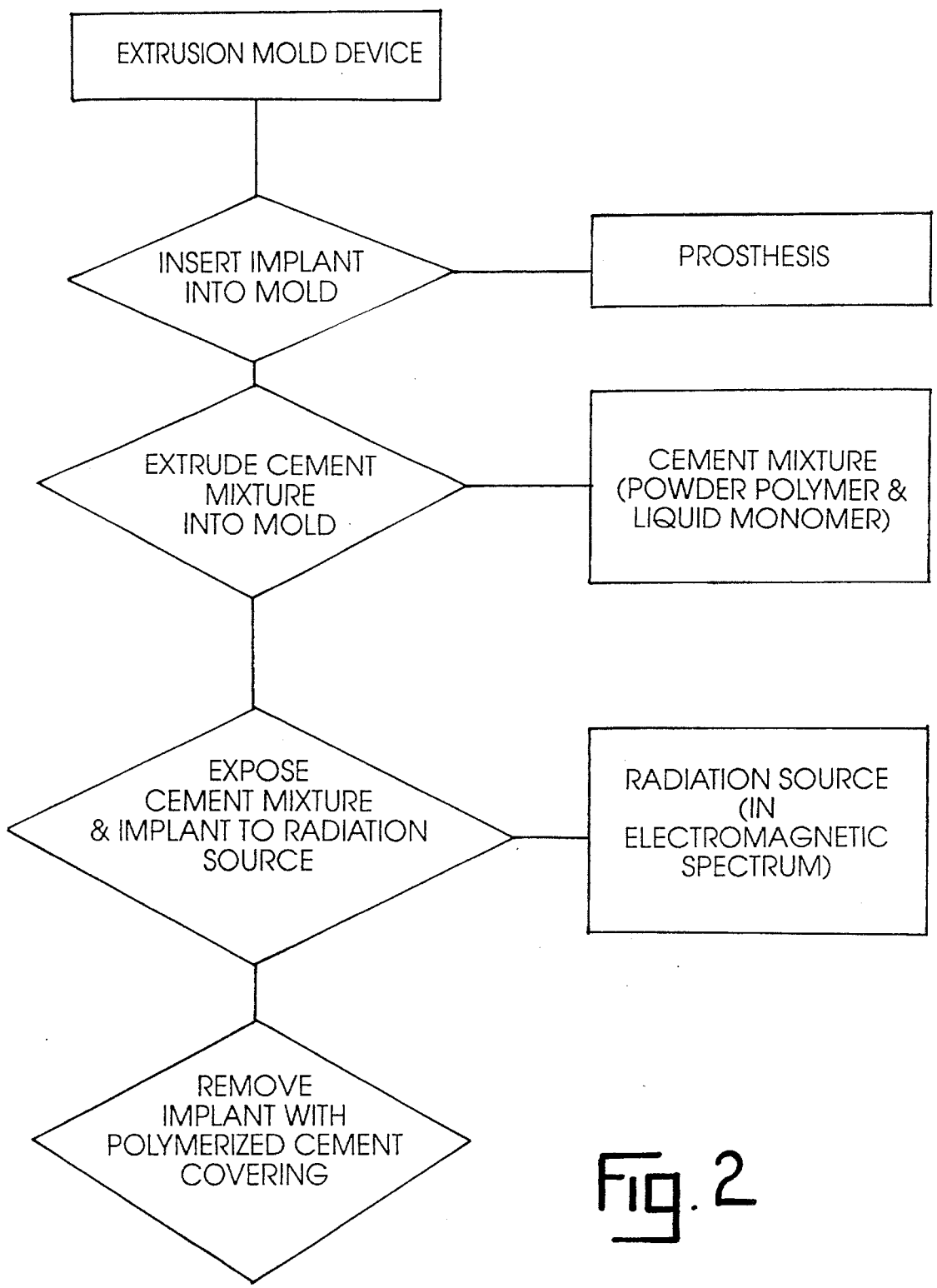
FIG. 2 is a flow chart of the method of this invention used in an extrusion process.

As shown in FIG. 2, the implant is first inserted into a suitable mold. The implant is fitted into the mold so that the cement mixture will cover a portion of the implant body. The mold is contoured to form the cement mixture to the intended outer geometry of the finished implant. Next, the flowable cement mixture is injected into the cavity of the mold under pressure to eliminate any voids. In the last step, the cement mixture within the mold is exposed to an source of radiation in the electromagnetical spectrum, such X-rays or gamma rays to initiate polymerization of the monomer in the cement mixture. Conventional radiation equipment, such as X-ray equipment used in medical application for diagnosis and industrial application for metal component inspection, can be used to directly expose the mold and cement mixture to radiation. Radiating the cement mixture creates free radicals in the monomer. The action of the free radicals commences the polymerization of the monomer. In addition, any benzoyl peroxide group which may be in the PMMA may provide an additional source of free radicals. The energy level of the radiation source and length of exposure is selected relative to the cumulative mass of the monomer, the implant, the mold and the desired rate of polymerization.

Figure 3:
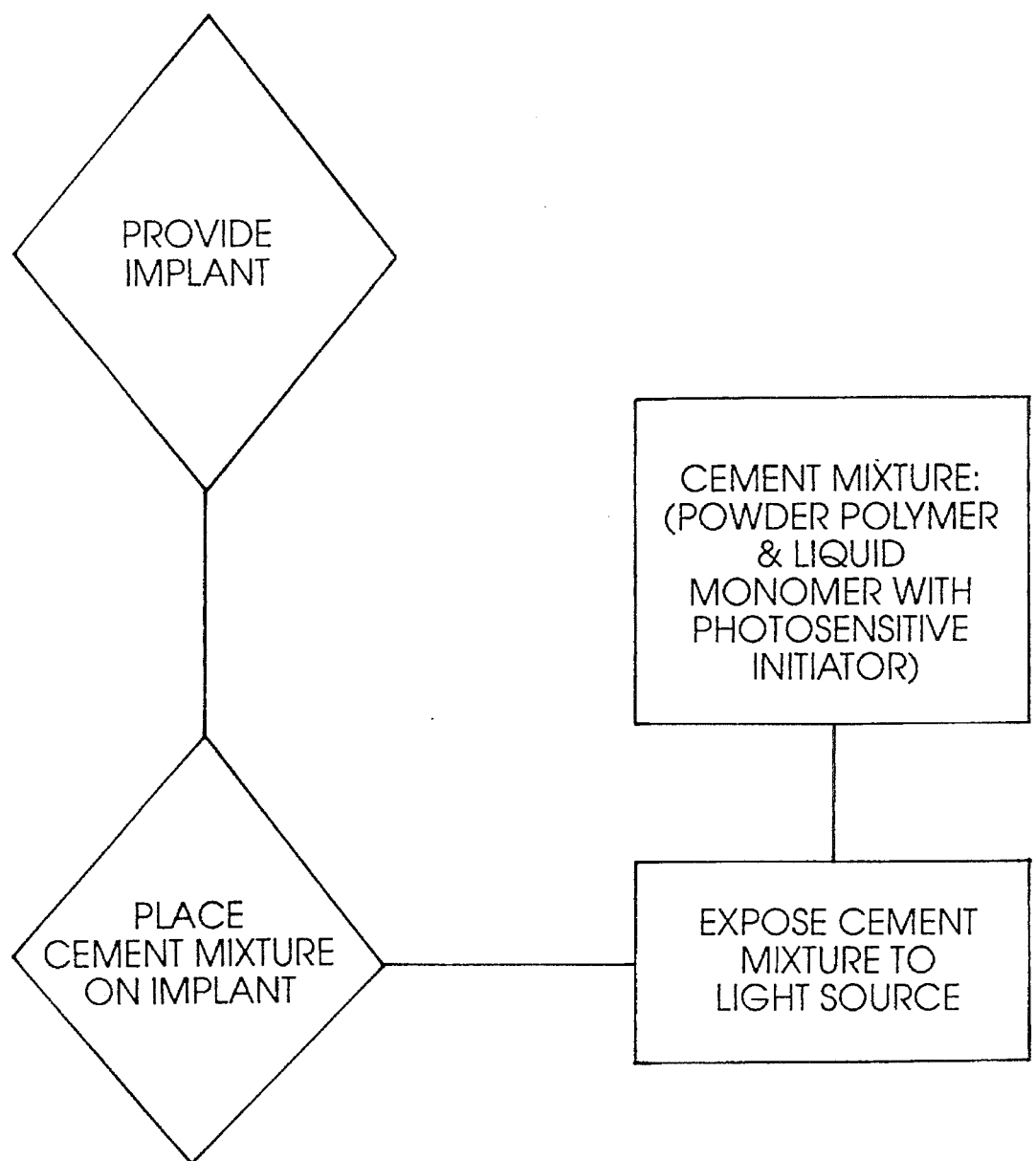
FIG. 3 is a flow chart of a second variation of the method of this invention used in an extrusion process.

FIG. 3 diagrams another variation of the method of this invention. In this variation, a light activated initiator is added to the cement mixture similar to the cement used in dental application to fill voids in teeth. The photosensitive initiator is added to the liquid monomer. Polymerization is initiated by exposing the mixture to a light source while in the mold through a transparent mold or while the cement mixture is being extruded into the mold. The exposure to the light source activates the photosensitive material to begin the polymerization.

It should be understood that while the specification generally refers to the process for molding cement to an implant, the term molding should be loosely interpreted. The cement mixture may infact be topically applied to an implant. Further, the cement mixture may be topically applied to the implant to act as an adhesive for a second component such as a pre-formed solid layer of cement.

It is understood that the above description does not limit the invention to the details given, but may be modified within the scope of the following claims.

I claim:

1. A method for molding a bone cement mixture to an implant comprising the steps of:
   a. providing a mold having a cavity,
   b. fitting said implant within said cavity;
   c. introducing said bone cement mixture in a fluid state into said cavity about said implant, said bone cement mixture includes a liquid monomer;
   d. exposing said bone cement mixture to a radiation source in the electromagnetic spectrum to initiate polymerization of said liquid monomer whereby said bone cement hardens to said implant.

2. The method of claim 1 wherein said radiation source in step c is gamma ray radiation.

3. The method of claim 1 wherein said radiation in step c is X-ray radiation.

* * * * *